(12) United States Patent
Lestician

(10) Patent No.: US 7,612,492 B2
(45) Date of Patent: Nov. 3, 2009

(54) LIGHTING APPARATUS AND SYSTEM FOR DECONTAMINATION

(75) Inventor: Guy J. Lestician, East Stroudsburg, PA (US)

(73) Assignee: Inventive Holdings LLC, Manalapan, NJ (US)

( * ) Notice: Subject to any disclaimer, the term of this patent is extended or adjusted under 35 U.S.C. 154(b) by 968 days.

(21) Appl. No.: 10/862,495

(22) Filed: Jun. 7, 2004

(65) Prior Publication Data

US 2005/0025662 A1 Feb. 3, 2005

Related U.S. Application Data

(60) Provisional application No. 60/476,494, filed on Jun. 6, 2003.

(51) Int. Cl.
*H01J 1/62* (2006.01)
*B01J 19/12* (2006.01)

(52) U.S. Cl. ..................... 313/483; 422/186

(58) Field of Classification Search ............... 313/637, 313/13, 158, 483; 422/24, 186; 250/455.11
See application file for complete search history.

(56) References Cited

U.S. PATENT DOCUMENTS

| | | | |
|---|---|---|---|
| 3,621,458 A * | 11/1971 | Amado et al. ............... 372/70 |
| 4,184,076 A | 1/1980 | Kosnoff | |
| 4,698,547 A * | 10/1987 | Grossman et al. ........... 313/485 |
| 5,287,040 A | 2/1994 | Lestician | |
| 5,364,645 A | 11/1994 | Lagunas-Solar et al. | |
| 5,387,400 A | 2/1995 | Pelster | |
| 5,393,419 A | 2/1995 | Tiede et al. | |
| 5,451,791 A | 9/1995 | Mark | |
| 5,494,576 A | 2/1996 | Hoppe et al. | |
| 5,626,768 A | 5/1997 | Ressler et al. | |
| 5,920,075 A | 7/1999 | Whitehead | |
| 5,925,986 A | 7/1999 | Moisin | |
| 6,039,928 A | 3/2000 | Roberts | |
| 6,129,893 A | 10/2000 | Bolton et al. | |
| 6,132,784 A | 10/2000 | Brandt et al. | |
| 6,264,888 B1 | 7/2001 | Palestro et al. | |
| 6,268,200 B1 | 7/2001 | Tucker et al. | |
| 6,277,337 B1 | 8/2001 | Goodrich, Jr. et al. | |
| 6,468,433 B1 | 10/2002 | Tribelski | |
| 6,483,119 B1 | 11/2002 | Baus | |
| 6,497,840 B1 | 12/2002 | Palestro et al. | |
| 6,503,458 B1 | 1/2003 | Ogle | |

(Continued)

FOREIGN PATENT DOCUMENTS

EP 0 577 975 A1 1/1994

OTHER PUBLICATIONS

"2002 Annual Water-Quality Report," the Municipal Authority of the Borough of West View, West View Water Authority (PWS ID No. PA5020043).

(Continued)

*Primary Examiner*—Joseph L Williams
(74) *Attorney, Agent, or Firm*—Pepper Hamilton LLP

(57) ABSTRACT

Contamination is reduced by exposing a specimen to light, such that the light includes ultraviolet and light of wavelength in the visible region, so that the light in the visible region damages the shell of an organism and the ultraviolet light prevents reproduction of the organism.

13 Claims, 16 Drawing Sheets

U.S. PATENT DOCUMENTS 6,528,021 B1     3/2003    Williams
2002/0174674 A1    11/2002    Takahashi et al.

OTHER PUBLICATIONS

Myron Lupal, "UV Offers Reliable Disinfection," (http://www.cwqa.com/html/UV_Article.htm), 5 pages.

"Ultraviolet Treatment for Drinking Water," Purewater 4U Store, Drinking Water Systems & Replacement Filters, (http://www.purewater4u.com/freeinfo/UV.shtml, 7 pages.

"Ultraviolet: The Science Behind the Medicine," (http://www.clarionhealth.com/clarion/science/science.html), Copyright 2000, 12 pages.

* cited by examiner

US 7,612,492 B2

LIGHTING APPARATUS AND SYSTEM FOR DECONTAMINATION

RELATED APPLICATIONS

This application claims priority to, and incorporates by reference, U.S. provisional patent application No. 60/476,494, filed Jun. 6, 2003.

TECHNICAL FIELD

The present invention relates to methods and systems for decontamination. More specifically, the present invention relates to methods and systems using lighting at various frequencies and/or wavelengths to destroy spores, bacteria, other microorganisms or other living organisms such as cells or mites.

BACKGROUND

Deadly or otherwise harmful spores, viruses and other bacteria plague our environment. Many technologies have arisen to respond to this problem. For example, to eliminate and/or reduce the growth of bacteria in foods, various methods of irradiating food have been developed. Deadly and/or disease-causing spores can be found in other locations as well, as demonstrated by the discovery of anthrax and various letters sent through the United States mail. Such spores, bacteria, viruses and microorganisms can spread naturally, such as through normal daily human contact, or they can be introduced artificially, such as through terrorism or other human intervention.

Prior methods to eliminate and/or prevent the growth of such microorganisms typically include the use of high power radiation to kill the microorganisms. Ultraviolet light, and in particular UV-C light having a wavelength of approximately 254 nm, is known to damage the DNA of bacteria, viruses and other pathogens by forming covalent bonds between adjacent thymine bases in their DNA. This action prevents the organism from reproducing. Thus, some systems have used ultraviolet light to provide decontamination effects. Other systems, such as that described in U.S. Pat. No. 6,268,200, have used microwave energy to achieve similar results. In each case, such systems typically require high power and/or long exposure to the light for decontamination to occur, and they are not effective to kill many types of organisms.

Accordingly, an improved system and method for destroying unwanted organisms is desired.

SUMMARY OF THE INVENTION

In an embodiment, one or more lamps capable of emitting light of various frequencies and/or wavelengths are used to destroy organisms. An electronic controller, such as an Electronic Ballast Bursting Unit™ ("EBBU™"), may be used to adjust the wavelength of the light emitted by the lamps based on the type of organism to which the light will be administered in an embodiment.

In another embodiment, a method of reducing contamination includes exposing a specimen to ultraviolet light and exposing the specimen to light at one or more selected wavelengths in the visible region. The irradiance of the light at the one or more selected wavelengths in the visible region will be sufficient to accelerate damage to one or more organisms in or on the specimen, typically, by opening a skin, outer membrane or other shell of the one or more organisms. The one or more selected wavelengths in the visible region may be selected based on the one or more organisms for which contamination reduction is desired. The exposure to ultraviolet light and the exposure to visible light may occur simultaneously. The ultraviolet light may comprise light at a wavelength of approximately 254 nm. Optionally, the method may include simultaneously exposing the specimen to light at one or more wavelengths below 200 nm at an intensity sufficient to produce ozone.

In an alternate embodiment, a decontamination system includes a power source, a lighting controller, and one or more ultraviolet lamps. When controlled by the lighting controller, the lamps will emit ultraviolet and visible light. The visible light will include light at one or more selected wavelengths at intensities sufficient to accelerate damage to an organism exposed to the light. The lamps may be made of quartz glass, and in an embodiment they may contain a gas mixture of at least argon and krypton, although any germicidal gas mixture may be used in other embodiments. The controller may include a frequency generator that adjusts the irradiance of the light emitted at one or more of the wavelengths so that the adjusted intensities of the light emitted at the selected wavelengths are near the intensity of the emitted ultraviolet light. For example, the frequency generate may be a pulse width modulator. Optionally, the controller includes one or more transformers having at least one winding comprising multistranded wire.

In an alternate embodiment, a lighting controller includes a frequency generator and an output to receive and deliver power to one or more lamps. The frequency generator adjusts the frequency of a signal delivered to the output so that, when the output is connected to one or more bulbs, the bulbs emit radiation at a frequency that will crack the shell of an organism. The output also delivers power to the one or more bulbs so that the one or more bulbs will emit light at approximately 254 nm.

DETAILED DESCRIPTION

Figure 1:
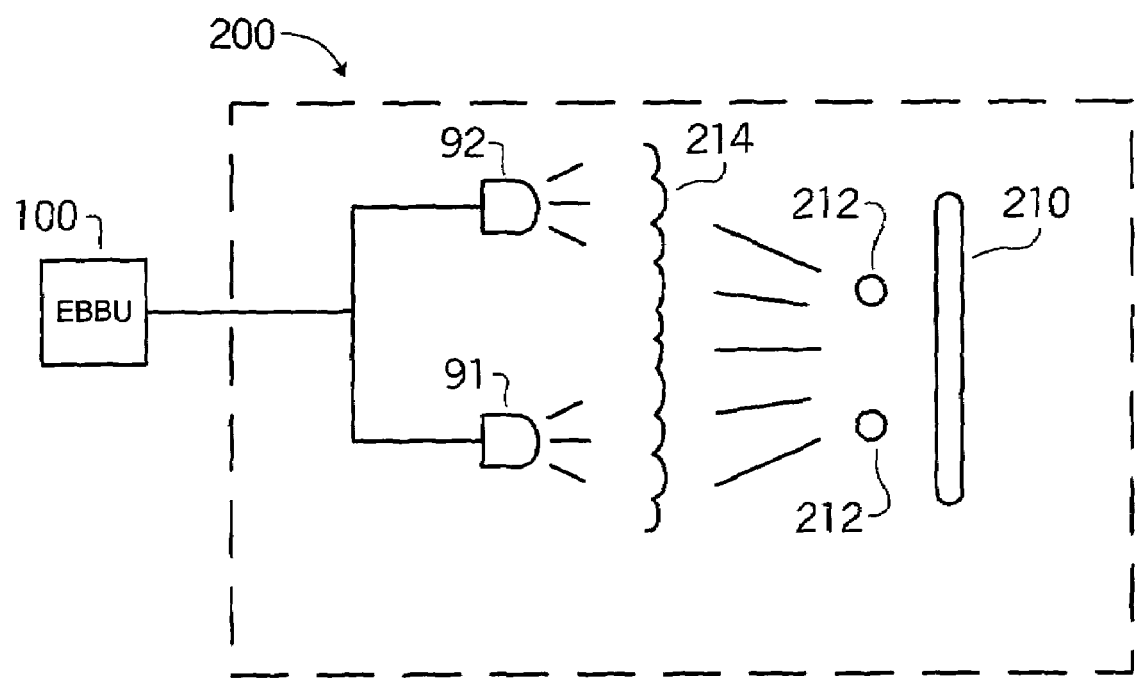
FIG. 1 is a block diagram illustrating exemplary elements of an Electronic Ballast Bursting Unit ("EBBU"), lamp(s) and enclosure, optional diffuser, treating area and specimen(s) to be decontaminated.

Referring to FIG. 1, in a system embodiment of the present invention, an electronic controller, such as an electronic ballast bursting unit ("EBBU") 100 may be used to deliver and adjust the frequency of power delivered to one or more ultraviolet lamps 91 and 92. The lamps may be situated under a hood or in an enclosure 200 that includes the treating area 210. One or more objects 212 that are to be decontaminated may be placed or passed under or near the bulb(s) and travel through or sit within the treating area. Optionally, the treating area 200 may include a hood with a light diffuser 214 made of materials such as honeycomb or angled reflective material to direct the light from the lamps into an area for treatment and minimize or prevent the diffusion or stray illumination of light. Optionally, the enclosure 200 may include a filter or shield to prevent the user's eyes from being damaged by the emission of light inside of the enclosure.

A specimen to be decontaminated is placed in proximity to the lamp or lamps, and the EBBU is used to deliver a wavelength of light that is appropriate to quickly and efficiently kill bacteria, spores or other organisms on or in the specimen.

Figure 2:
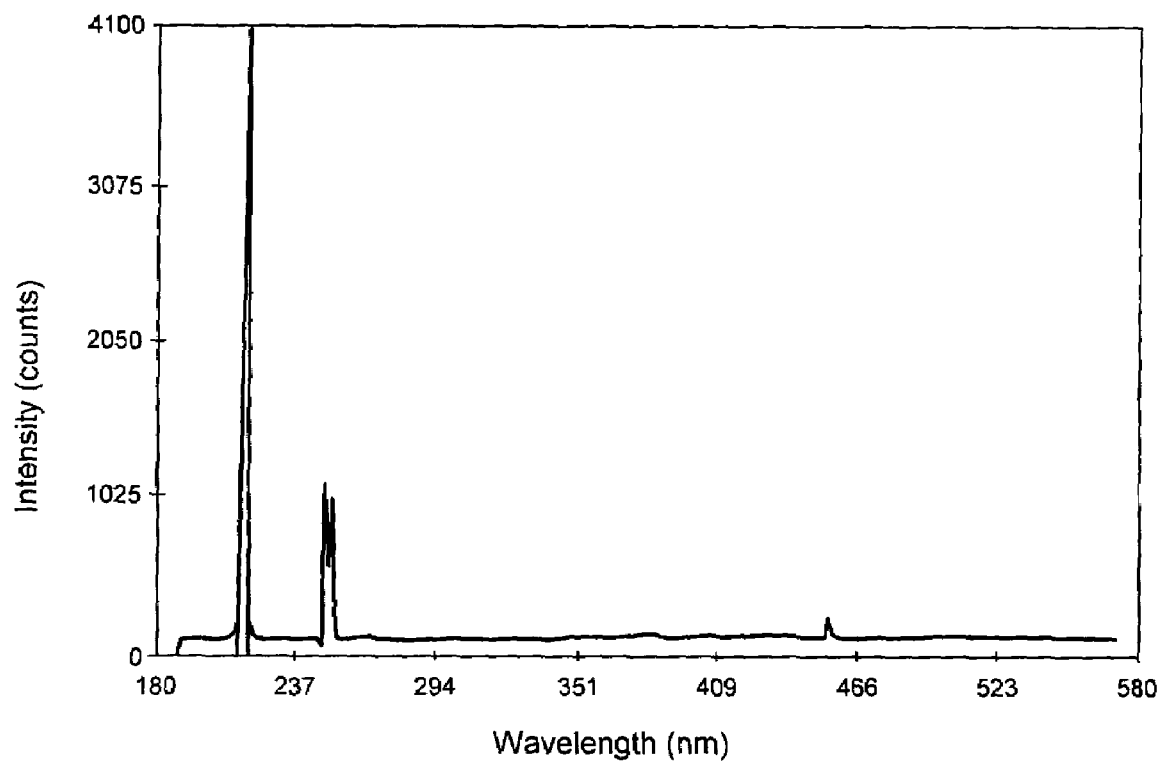
FIG. 2 illustrates exemplary light output of a standard ozone-providing germicidal bulb.

For example, as illustrated in FIG. 2, a standard ultraviolet bulb may deliver light at a wavelength at or near 254 nanometers (nm). In addition, an ozone-producing bulb may deliver light at lower wavelengths, such as 180 to 185 nm, which may produce ozone. The ozone and approximately 254 nm light are known to those skilled in the art to have germicidal properties.

Figure 3:
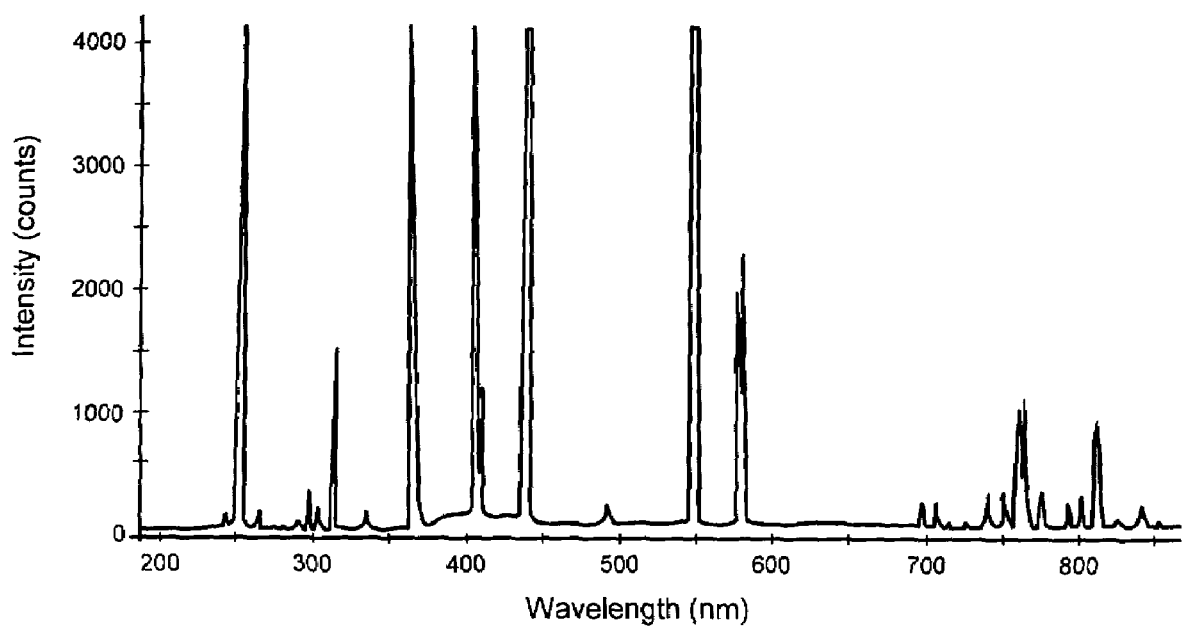
FIG. 3 illustrates exemplary output of a germicidal bulb in accordance with an embodiment of the present invention.
Figure 4:
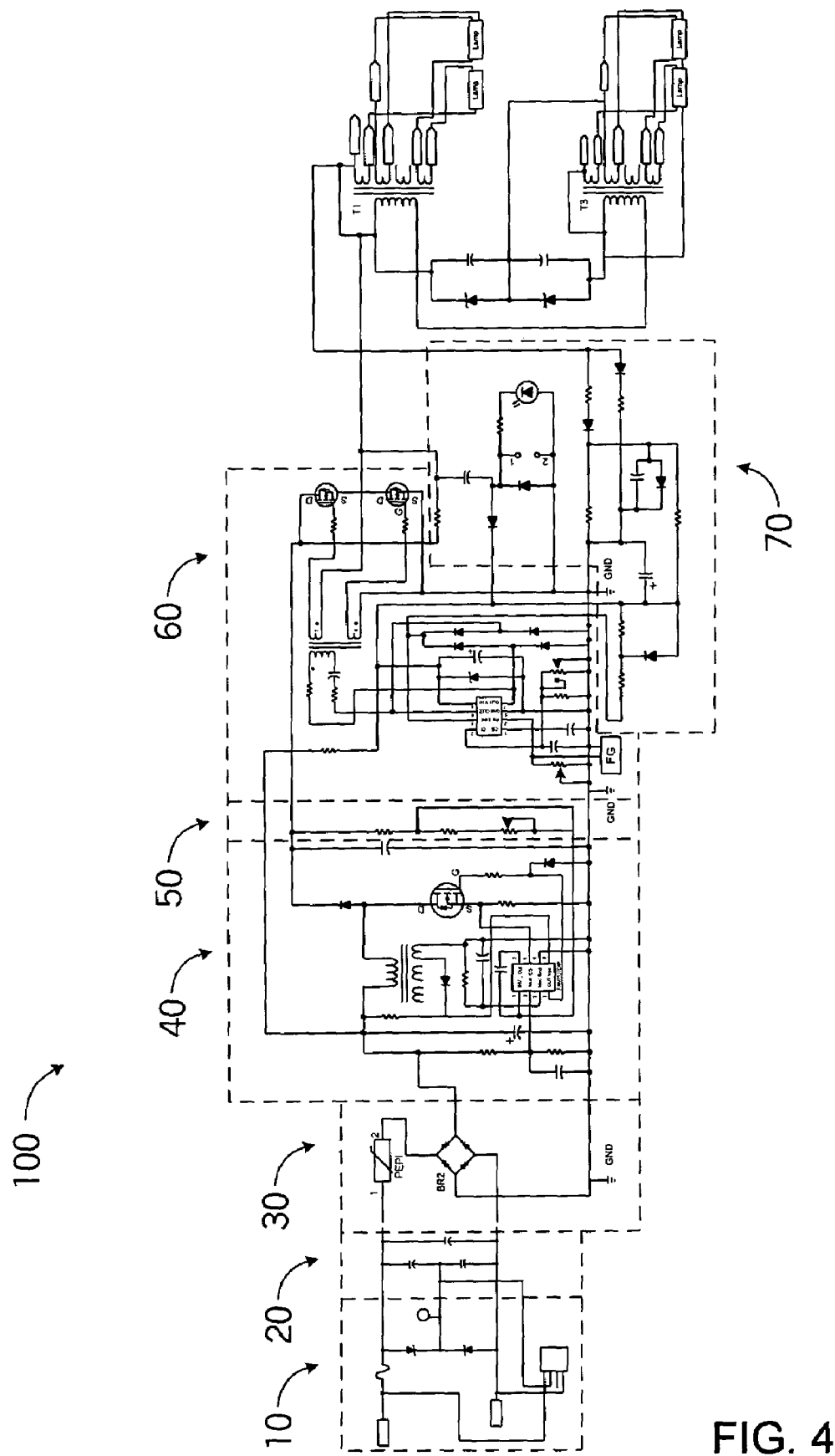
FIG. 4 illustrates an embodiment of an EBBU as it may be used to drive a group of fluorescent lamps.
Figure 5:
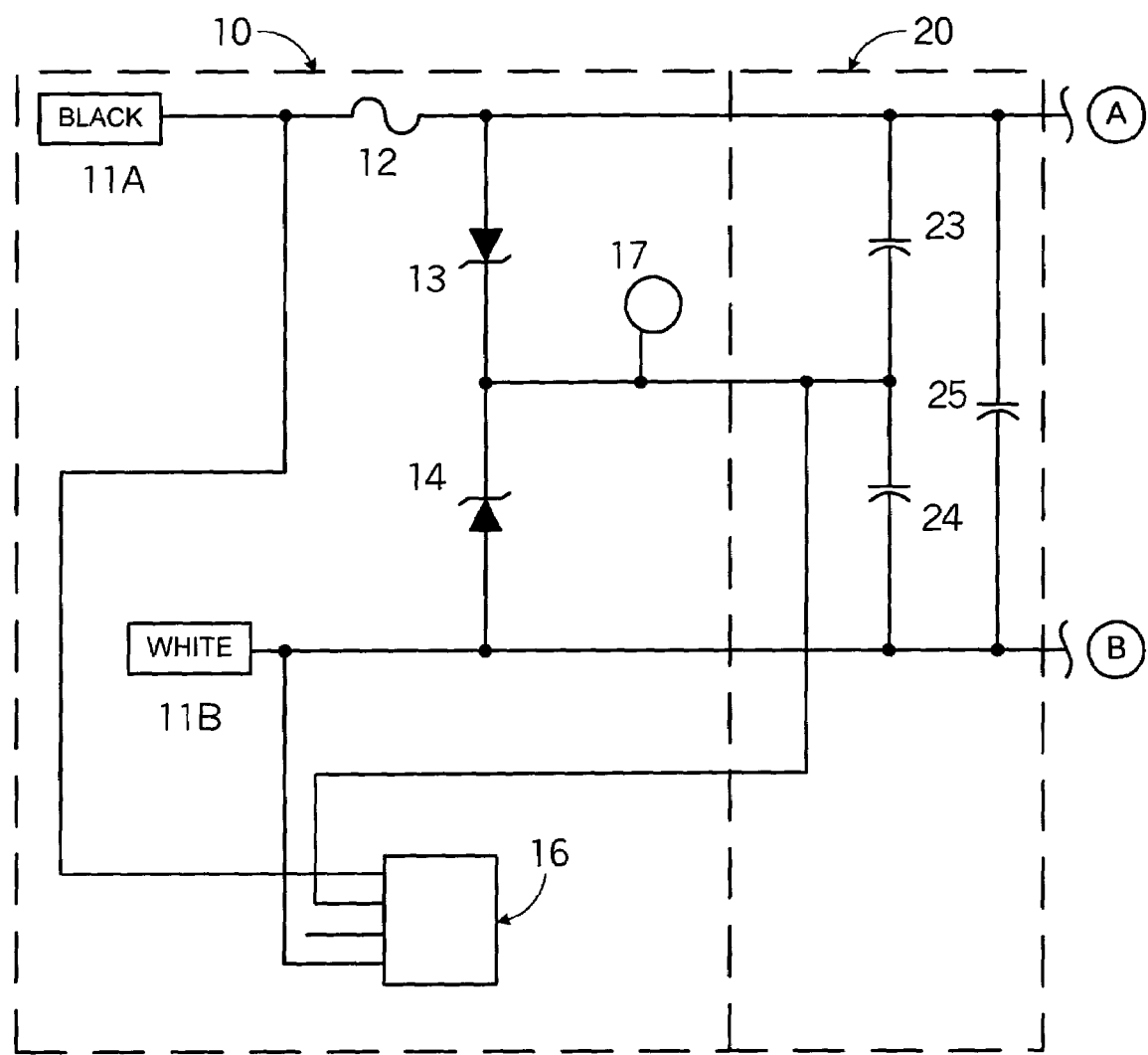
FIG. 5 illustrates input and filter stages of the embodiment of FIG. 5.
Figure 6:
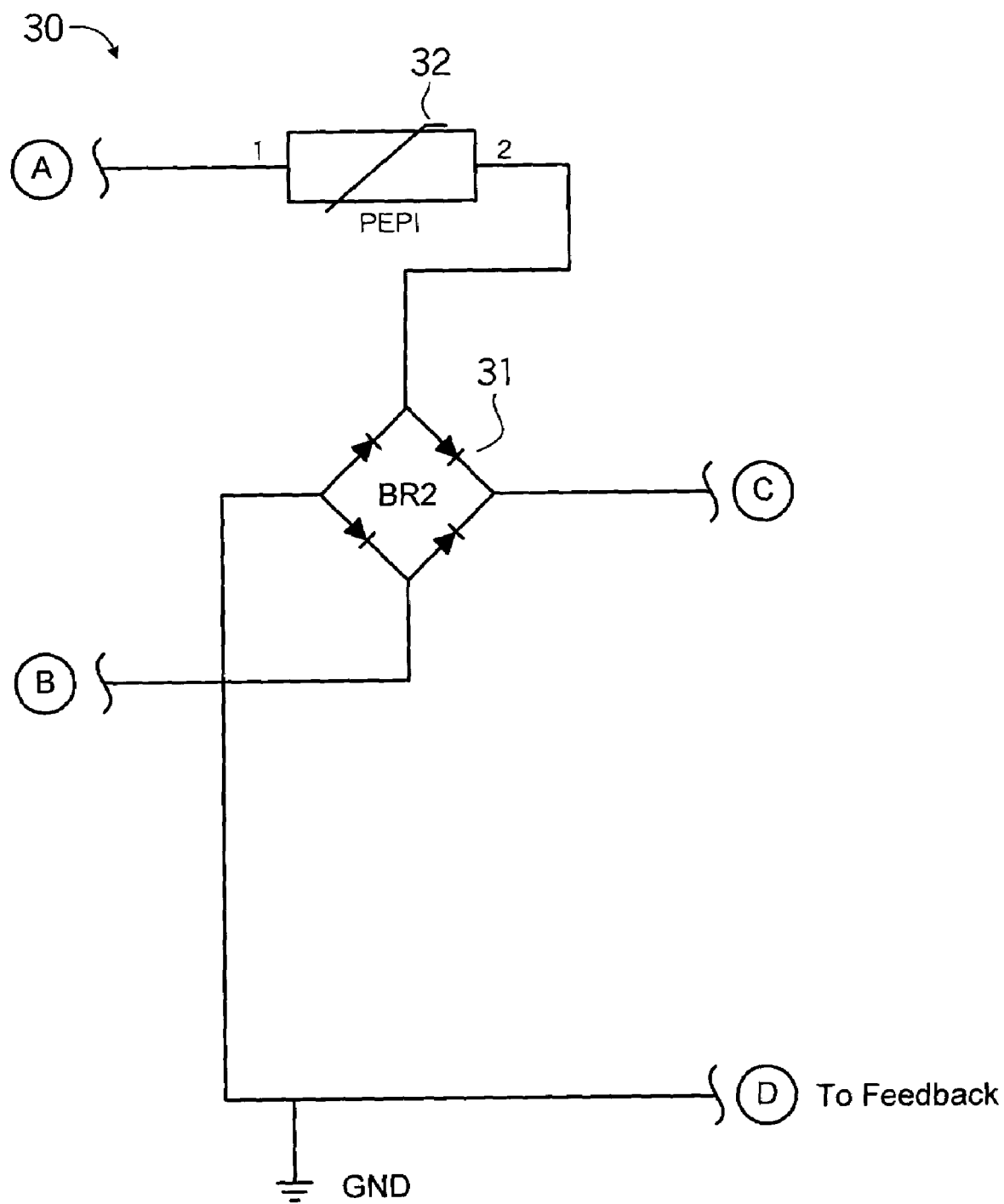
FIG. 6 illustrates elements of the DC rectifier stage of FIG. 4.
Figure 7:
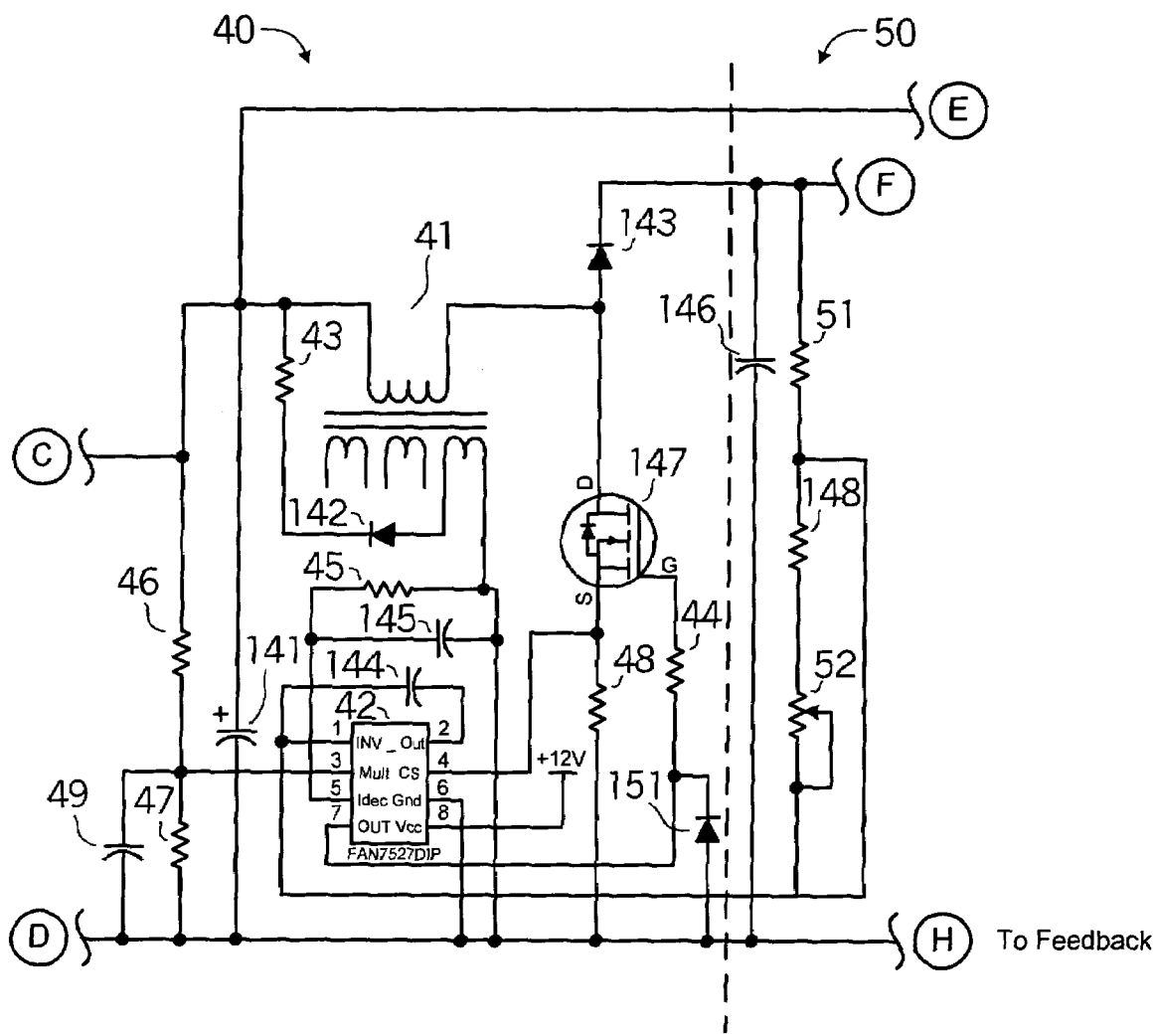
FIG. 7 illustrates exemplary elements of the power factor correction stage of FIG. 4.

Surprisingly and advantageously, I have found that increasing the intensity of light at higher wavelengths, and in particular specific wavelengths in the ultraviolet and visible regions, may accelerate and/or promote decontamination. In particular, while the prior art has taught that light in the visible region will not possess germicidal properties, I have found that certain focused visible light intensities may accelerate the germicidal activity of ultraviolet light. For example, as illustrated in FIG. 3, increasing the irradiance, or intensity of light at approximately 365 nm, 405 nm and 436 nm may significantly accelerate decontamination of *Bacillus atrophaeus* or *Bacillus stearothermophilus*, while increased irradiance at approximately 546 nm and 579 nm may accelerate decontamination of the niger virus. As shown in FIG. 3, some or all of these intensities may be increased to be substantially equal to the irradiance of 254 nm ultraviolet light from the bulbs.

An exemplary circuit diagram showing an embodiment of an EBBU is illustrated in FIG. 4. As indicated in FIG. 4, the EBBU 100 may include as many as seven stages or more, each of which provides additional features for the system.

Referring to FIG. 4, in the illustrated embodiment the first stage of the device 10 receives an input voltage and operates as an AC power supply. The input stage 10 may accept an input voltage that is at least between the range of 80 and 300 volts, although other voltages are possible depending on the load to be driven. The second stage 20 functions as electromagnetic interference (EMI) filter. The third stage 30 functions as a DC rectifier, converting the AC input voltage to a DC voltage, with a connection to a feedback circuit. The fourth stage 40 operates as a power factor correction stage. The fifth stage 50 operates as a high-voltage power filter. The sixth stage 60 operates as the output stage to deliver power to one or more bulbs or other devices. The seventh stage 70 is a general feedback stage. Although FIG. 4 as illustrated defines a boundary for the feedback stage 70, the boundary is only intended to illustrate a portion of the feedback stage 70. In fact, feedback may be provided to each of stages 30, 40, 50 and 60.

FIG. 5 through FIG. 13 provide additional detail of certain embodiments of the individual stages described above and illustrated in FIG. 4. The values listed below for individual elements are exemplary values only and should not be interpreted as limiting. Persons skilled in the art will recognize that other values are possible without departing from the spirit and scope of the invention. In addition, one skilled in the art will recognize that other circuits may be used to achieve similar results. Additional details of exemplary circuits are disclosed in the co-pending U.S. patent application entitled "Lamp Driver," filed Apr. 30, 2004, having Ser. No. 10/835,839, which is incorporated herein by reference in its entirety.

Exemplary elements of input stage 10 and second stage 20 are illustrated in FIG. 5. Referring to FIG. 5, input stage 10 includes a power source, optionally between 80 and 300 volts, or plug 16 at AC inputs 11A and 11B, a line fuse 12 such as a 4-amp fuse, and two varistors 13 and 14. In the illustrated embodiment, the power source may be a 120V, 60 Hz voltage source, and the line fuse 12 may be a 4 amp fuse for a driver for two 120-watt lamps. When the circuit is used to light higher intensity lamps or additional numbers of lamps (such as four 120-watt lamps), larger fuses may be needed. Varistors or zener diodes 13 and 14 may function as surge protection devices connected between each of the AC inputs and ground 17. When a power surge or voltage spike is exhibited on the AC inputs, the resistance of varistors or zener diodes 13 and 14 may quickly decrease, creating a shunt path for the overvoltage. In this way, other components in the device may be protected from power surges.

The EMI filter stage 20 of the device may function as a noise filter. In the filter stage, an LC filter may be replicated between each AC input 11A and 11B and ground. The LC filters operate as noise filters to remove unwanted frequencies from the AC voltage input source. The LC filters may, be composed of optional inductors 21 and 22 (not shown in FIG. 5), and capacitors 23 and 24. In an embodiment, the inductors 21 and 22 may have an inductance of approximately 600 nH, and capacitors 23 and 24 may have a capacitance of approximately 2.2 nF. Capacitor 25 may have a capacitance of 1.0 μF. Other values are possible without departing from the spirit and scope of the invention.

The DC rectifier stage 30 may convert the AC input signal into a DC signal. Exemplary elements of the DC rectifier stage 30 are illustrated in FIG. 6. Diode bridge 31 functions as a full wave bridge and converts the AC input voltage into a DC output voltage. Diode bridge 31 may be made of a full wave rectifier, or it may be four separate diodes, such as 4-amp diodes. The use of separate diodes instead of a rectifier is preferred when bulbs having a higher total wattage are used. Diode bridge 31 may be connected to the feedback stage 70 via the ground plane. The connection between diode bridge 31 and ground may stabilize the voltage differential across the bridge. Optional thermal cutout component 32 may operate as a temperature-sensitive, protective device to shut down the operation of diode bridge 31 in certain thermal conditions. For example, thermal component 32 may trigger a shut down when it senses an external temperature of 105° C., which may indicate a fire.

Exemplary elements of the power factor correction stage 40 are illustrated in FIG. 7. A coil device 41 operates to boost the output voltage based on the lamp or lamps (or other device or devices) attached to the output of device 100. A coil device 41 using multistranded wire is described in co-pending U.S. patent application Ser. No. 10/834,778, entitled "Coil Device", filed Apr. 29, 2004, which is incorporated herein by reference in its entirety. Other coil devices are possible without departing from the spirit and scope of the invention. The coil device preferably includes a secondary winding to allow it to serve as a transformer for the delivery of power to the bulb or bulbs. The power factor correction circuit may be used to make a nonlinear load operate like a resistive load by putting it into phase. In one embodiment used to power two 120-watt fluorescent bulbs, the power factor correction controller 42 may be a Fairchild Semiconductor FAN7527 or similar device. The power factor correction controller 42 may be used along with one or more resistors 44-48; one or more capacitors 49, 141 and 144; one or more diodes 142 and 143; a coil device 41; and MOSFET 145 to create a power factor correction circuit. In the embodiment corresponding to FIG. 4, resistors 43, 44, 45, 46, 47 and 48 may have values of approximately 180Ω, 10Ω, 22 kΩ, 2.2 MΩ, 27 kΩ, and 0.25Ω, respectively, while capacitors 49, 141, 144 and 145 may have values of approximately 1 nF 1 μF, 1 μF and 1 MF, respectively. The embodiment shown in FIG. 5 may also include a diode 151.

Figure 8:
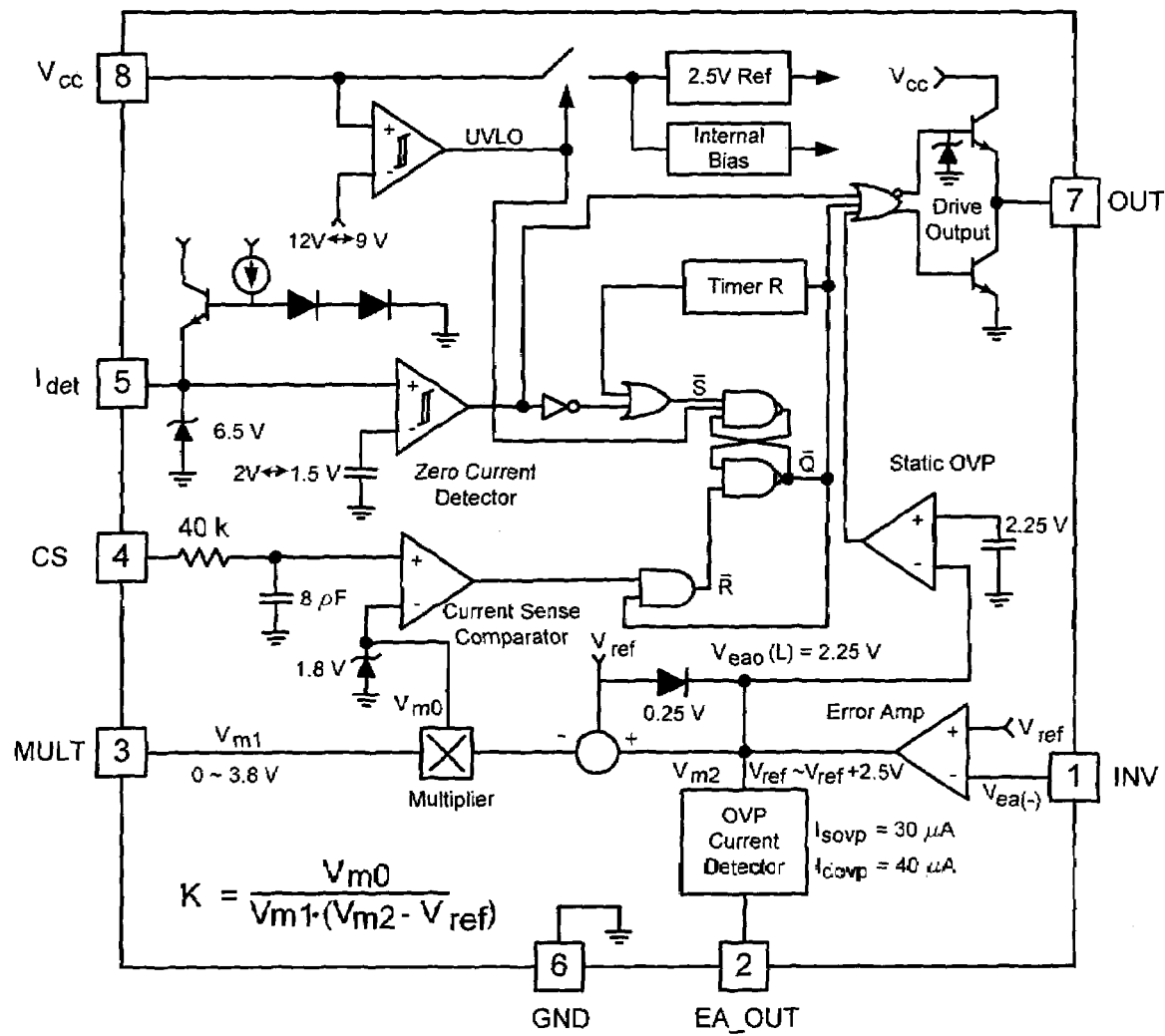
FIG. 8 is a block diagram of a prior art power factor correction circuit.

In the embodiment illustrated in FIG. 7, the power factor correction device 42 includes a two-stage power factor correction microchip. An example of such a microchip is the FAN7527B supplied by Fairchild Semiconductor. The two-stage microchip uses substantially the same frequency for pre-startup heating and actual startup, thus providing a power saving advantage. The operation of a prior power factor correction microchip is described in Fairchild Application Note AN4107, published May 2000, and is illustrated in FIG. 8.

Exemplary elements of a high voltage power filter stage 50 are also illustrated in FIG. 7. In one embodiment stage 50 may incorporate resistor 51 and variable resistor 52. In an embodiment, resistor 51 may have a resistance of about 1.1 MΩ, and variable resistor 52 may have a peak resistance of about 10 kΩ. The optional variable resistor 52 may be used to adjust the frequency of the output signal by changing its voltage, since a higher voltage will result in a higher frequency. A higher frequency of the output signal may also change the irradiance of one or more wavelengths of the light emitted by the bulb or bulbs. Optional resistor 148, such as a 6 kΩ resistor, may also be used.

Figure 9:
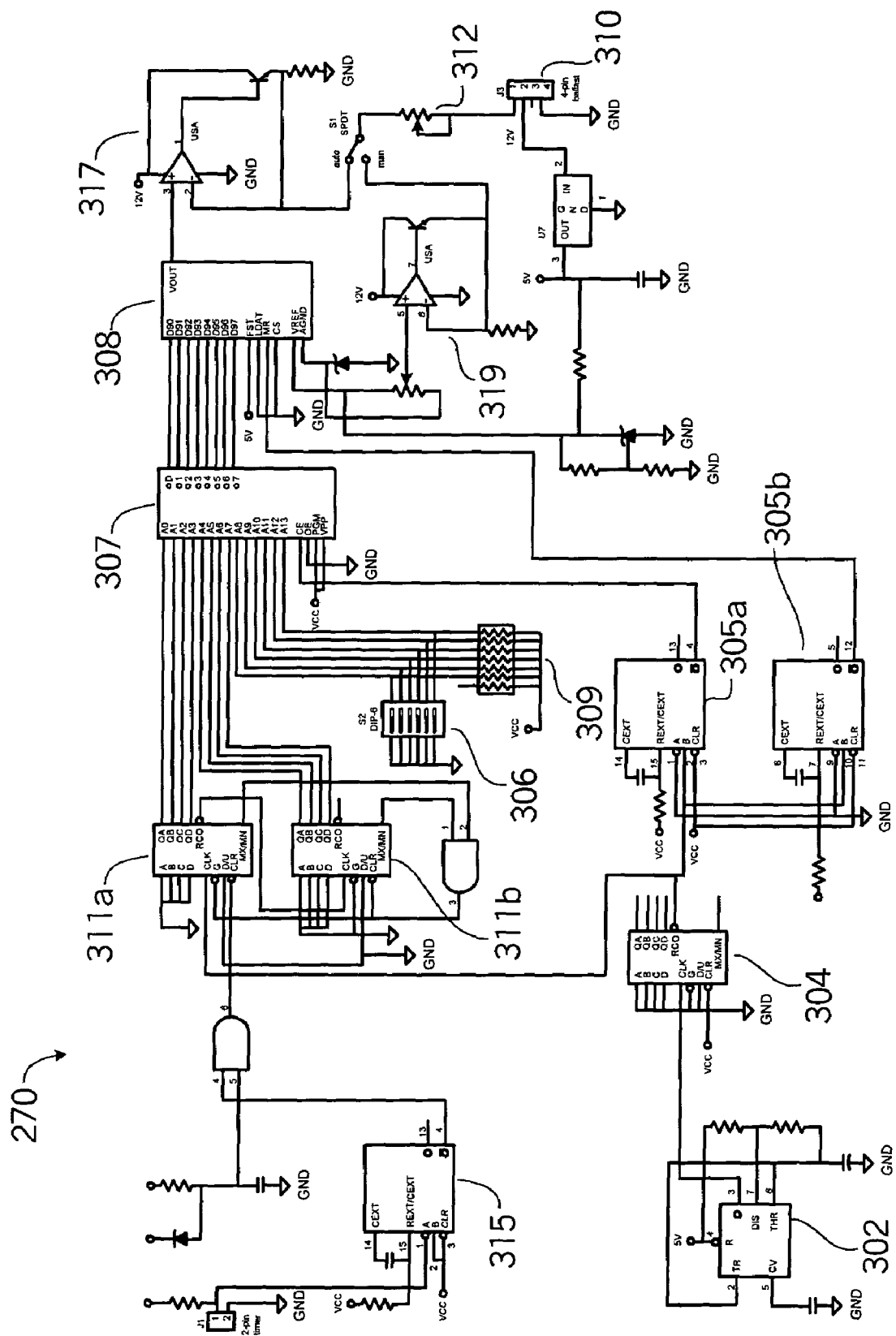
FIG. 9 is a block diagram of an exemplary frequency generator circuit.

In an alternate embodiment, the frequency may be adjusted using a frequency generator 270 such as an off-the-shelf or custom frequency generator. An exemplary off-the-shelf frequency generator is a Hewlett Packard HP8094 multi-function synthesizer. Alternatively, a frequency generation circuit such as that illustrated in FIG. 9 may be used. In the embodiment illustrated in FIG. 9, a timer 302 sets up a frequency and delivers a signal to a pre-settable synchronizable up/down counter such as a four-bit counter 304 set to provide a one-bit output every 30 seconds. The counter 304 induces a second frequency to allow mixture of two frequencies. One or more multiplexers 305a and 305b may also establish a time count for a digital-to-analog converter 307 and analog-to-digital converter 308 in the circuit. A switch such as a DIP switch 306 with optional pull-down resistors 309 may allow a user to adjust the accuracy of the injected frequency. The signals are delivered through analog-to-digital converter 307 and digital-to-analog converter 308 to a lamp driver output 310. Optionally, a variable resistor 312 may allow further adjustment of the frequency before it is delivered to the lamp driver. One or more decimal decoders 311a and 311b may act as counters, a switch 315, and one or more comparators 317 and 319 may also be present.

Figure 10:
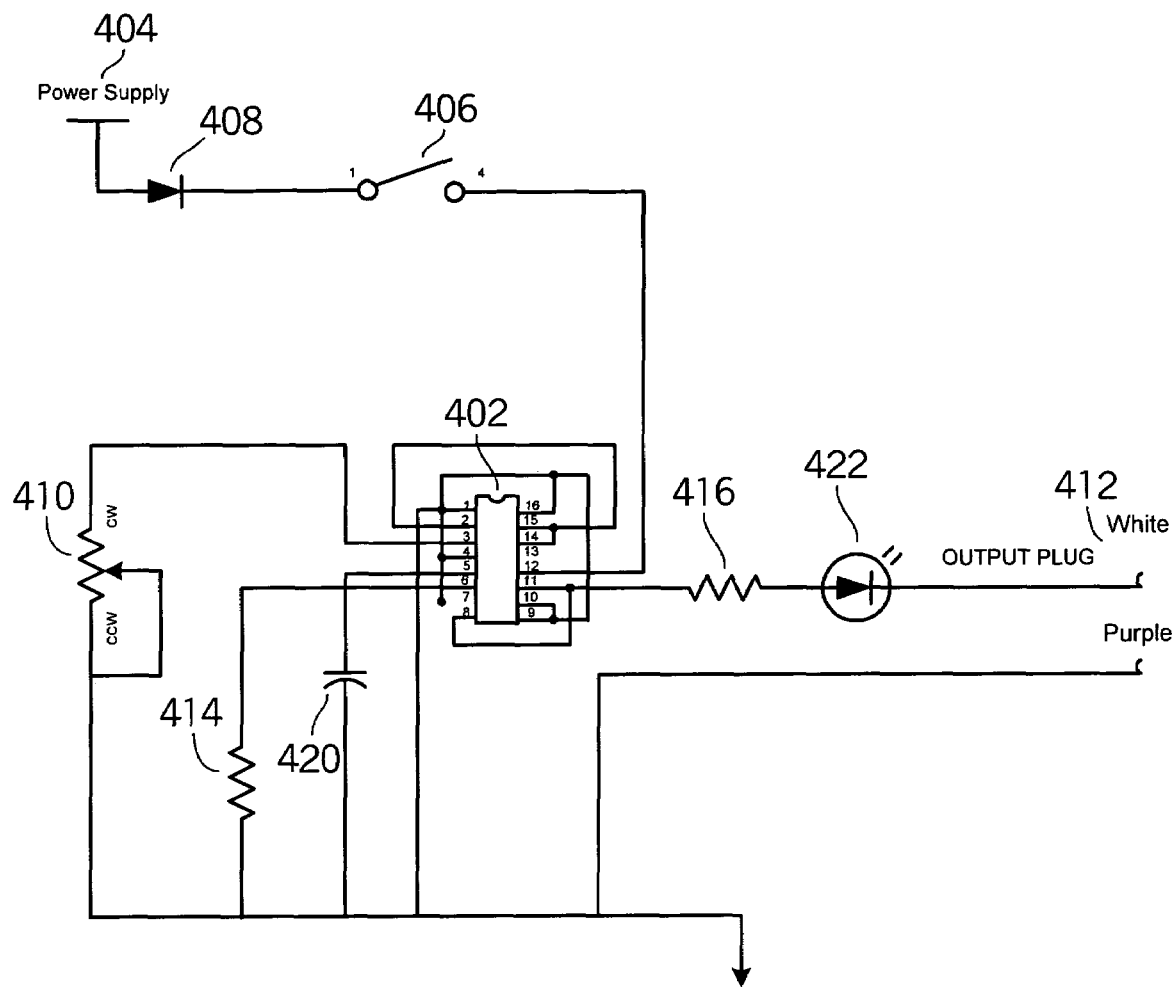
FIG. 10 is a block diagram of an alternate frequency injection circuit.

An alternate frequency injection circuit is illustrated in FIG. 10. Referring to FIG. 10, a pulse width modulator (PWM) 402 such as a Texas Instruments TL594 chip receives power from a power supply 404 with an optional switch 406 and diode 408 for controlling the circuit. With a variable resistor 410 such as one having a range of up to 5 KΩ, the PWM may be used to adjust and control the frequency delivered to an output 412, which is connected to the EBBU. Resistors 412 and 416 and capacitor 420 may have values of 19.1 KΩ, 1 KΩ, and 0.047 μF, respectively. Other values are possible. Optional light-emitting diode 422 may indicate when the circuit is powered.

Referring again to FIG. 7, capacitor 146 illustrated in FIG. 7 may have a resistance of between 47 MF and 100 MF. Other values are possible. In either embodiment (i.e., with a variable resistor or a frequency injector), the frequency of the output signal may be varied so that the lamp or lamps connected to the output of the ballast device emit light having increased irradiance at one or more focused wavelengths, selected based on the attributes of the bulb or bulbs to be driven and the organism for which decontamination is desired. Exemplary wavelengths are described in more detail below.

Figure 11:
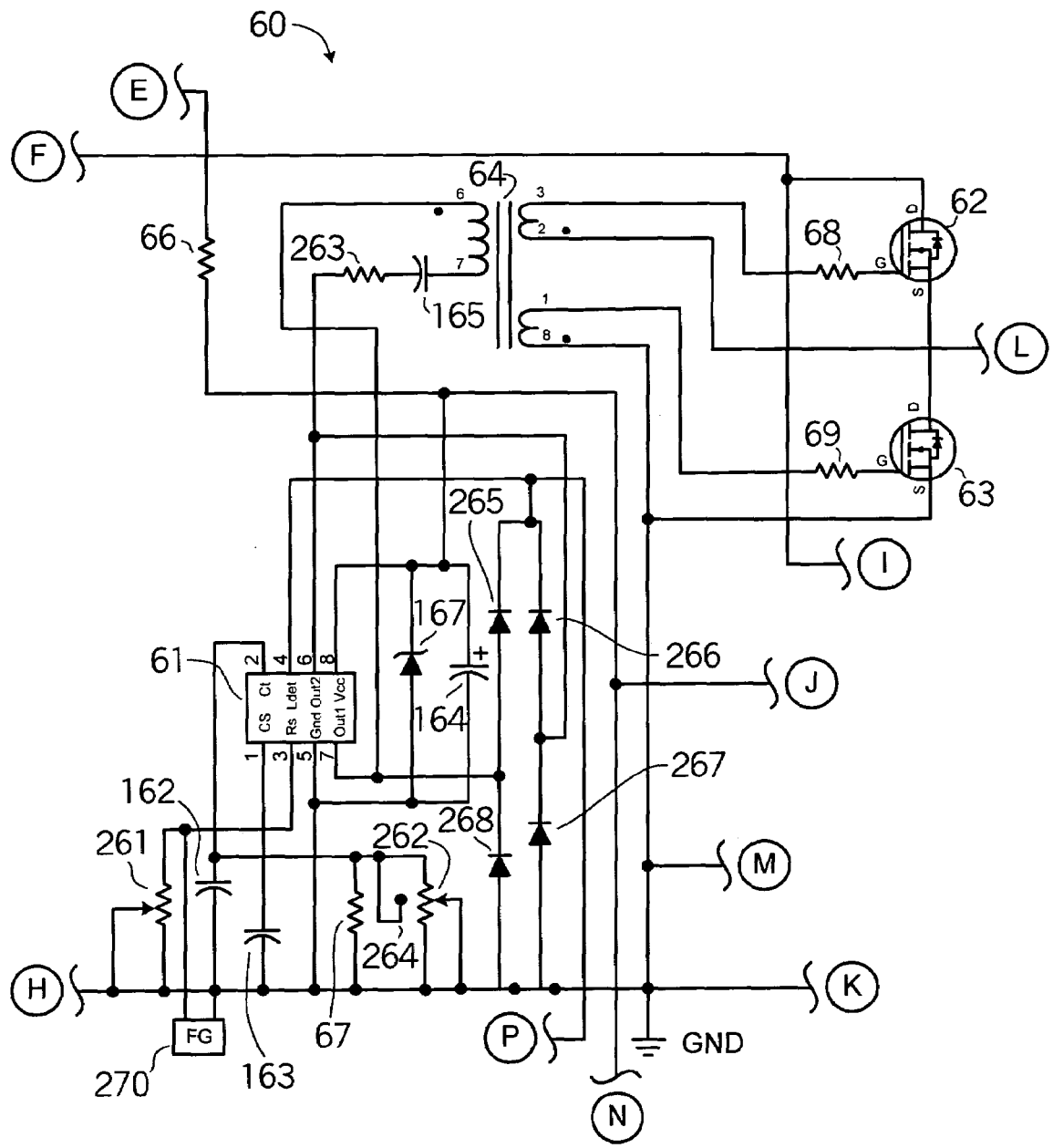
FIG. 11 illustrates exemplary elements of the output stage of FIG. 4.

Exemplary elements of an output stage 60 are illustrated in FIG. 11. Referring to FIG. 11, a controller 61 may be implemented by a ballast controller such as a Fairchild Semiconductor KA7540 or KA7541 or a similar device. The controller 61 may be used to produce the high output voltage required to drive the output MOSFETs 62 and 63 in conjunction with a standard gate driver 64. The MOSFETs 62 and 63 may blend the injected frequency component output from stage 50 or the optional frequency injector 270 and the high voltage driven from the standard gate driver 64 to produce the proper signal to the lamps and/or bulbs. The drain port of MOSFET 62 may be driven by stage 50 at a high voltage (such as 400 volts), and it may receive a pulse input at a frequency determined by the variable resistor 52 or frequency generator 270. The resulting output of MOSFETs 62 and 63 may be a DC square wave or substantially square wave.

Preferred, although not required, values for various elements in FIG. 11 are that resistors 263, 66, 67, 68 and 69 may be approximately 51Ω, 150 KΩ, 22 KΩ, 51Ω and 51Ω, respectively. Variable resistors 261 and 262 may each have values of between 1 KΩ and 100 KΩ. Capacitors 162, 163, 164, and 165 may be approximately 56 pF, 0.22 μF, 47 MF, and 0.22 μF, respectively. Varistor 167 may be a 15 volt Zener diode. Diodes 265, 266, 267 and 268 may be, for example, 300 volt diodes. In each case, other values are possible.

The use of a Fairchild Semiconductor KA7541 as controller 60 is illustrated in FIG. 11. However, in an alternate embodiment, a different controller 61 may be used.

Figure 12:
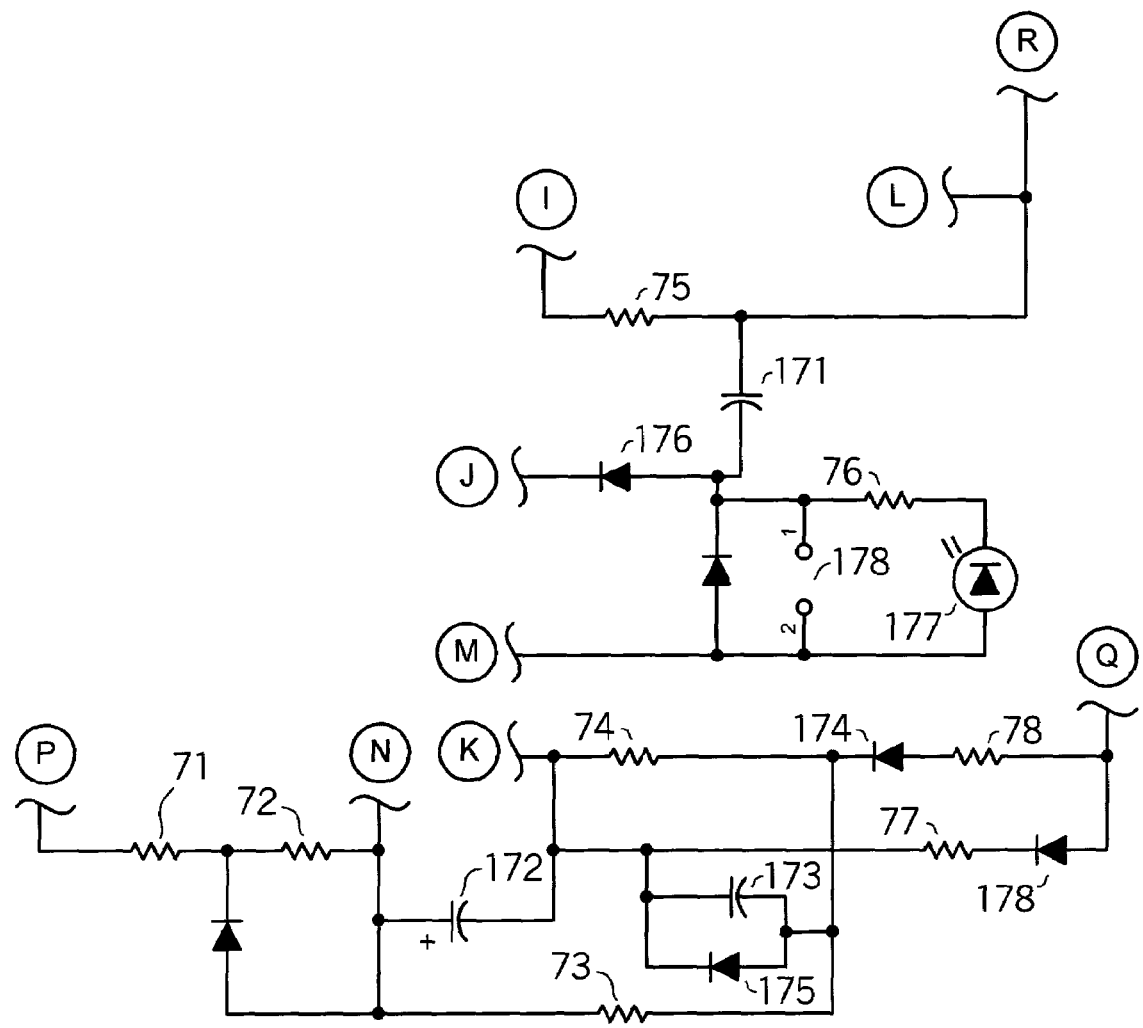
FIG. 12 illustrates an embodiment of the feedback stage of FIG. 4.

Referring to FIG. 12, feedback stage 70 is a general feedback stage in which the output voltage level is transmitted to other stages to permit for corrections in the total voltage differential in the circuit. Referring to FIG. 12, exemplary values for resistors 71, 72, 73, 74, 75, 76, 77 and 78 may be 10 KΩ, 10 KΩ, 442 KΩ, 220 KΩ, 150 KΩ, 10 KΩ, 200 KΩ and 442 KΩ, respectively, while exemplary values of capacitors 171, 172, and 173 may 0.22 nF, 1 mF and 1 μF, respectively. Other values are possible. The feedback stage 70 may also serve as a circuit to turn off MOSFETs 62 and 63 when no bulbs are not installed in the system. Although FIG. 12 illustrates a boundary for the feedback stage 70, the boundary is only intended to illustrate a portion of the feedback stage 70. In fact, feedback may be provided to each of stages 30, 40, 50 and 60.

Figure 13:
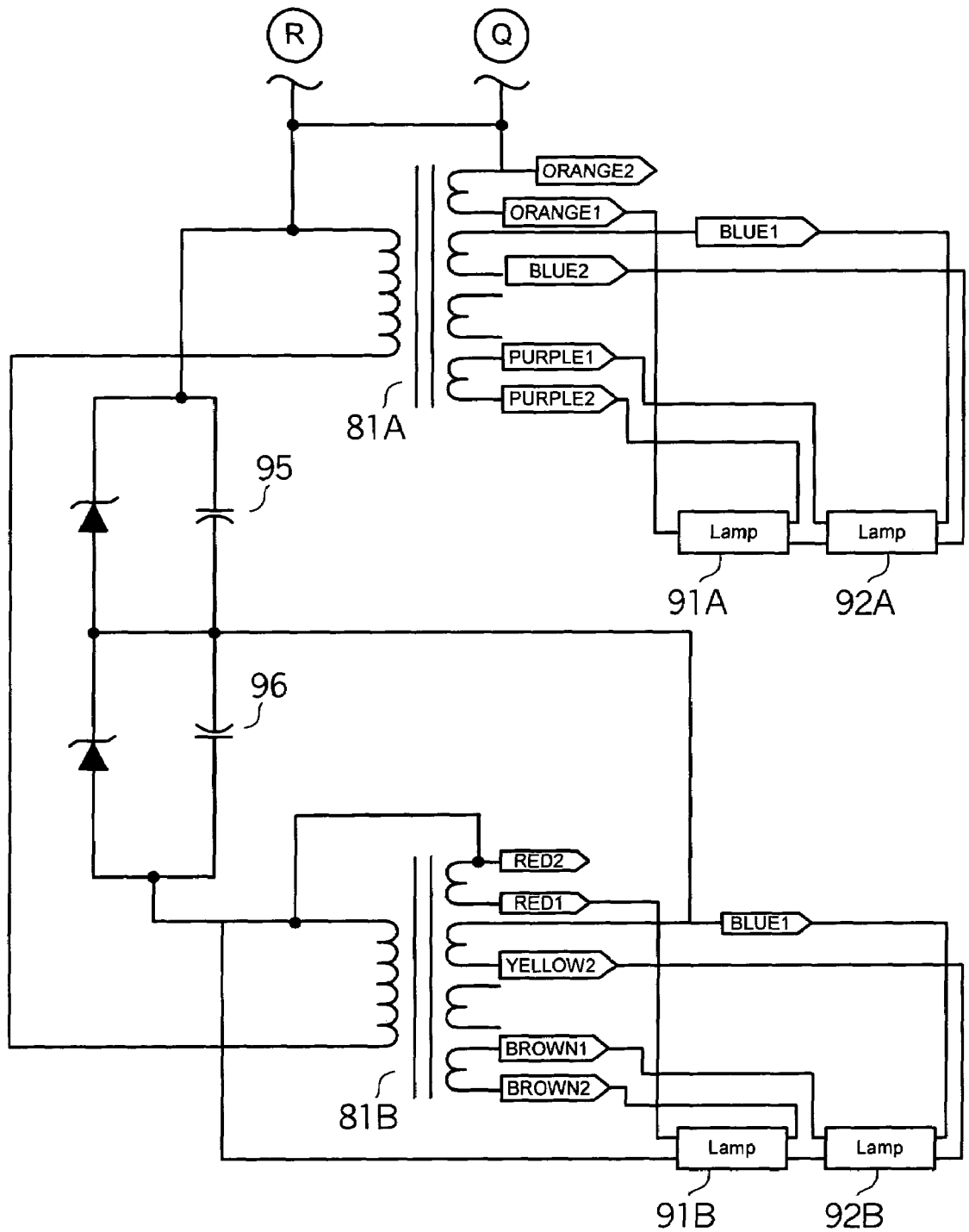
FIG. 13 illustrates further features showing the output being used to drive a fluorescent lamp.

The output waveform of the device may drive one or more bulbs to produce light having increased intensities at one or more desired wavelengths. Referring to FIG. 13, if one or more fluorescent bulbs 91A and 92A are driven, a coil device 82 similar to the one illustrated in stage 40 may be used to convert the DC square wave output from stage 60 of the ballast device into an AC sine wave. An exemplary coil device 82 is a multistranded wire device with a secondary winding as illustrated in pending U.S. patent application Ser. No. 10/834,778, filed Apr. 29, 2004, entitled "Coil Device", which is incorporated herein by reference in its entirety.

If two or more fluorescent lamps are connected, they may be connected in series as illustrated in FIG. 13. Each combination of two fluorescent lamps preferably has a single associated coil device. Additional configurations with additional lamps are possible.

Figure 14:
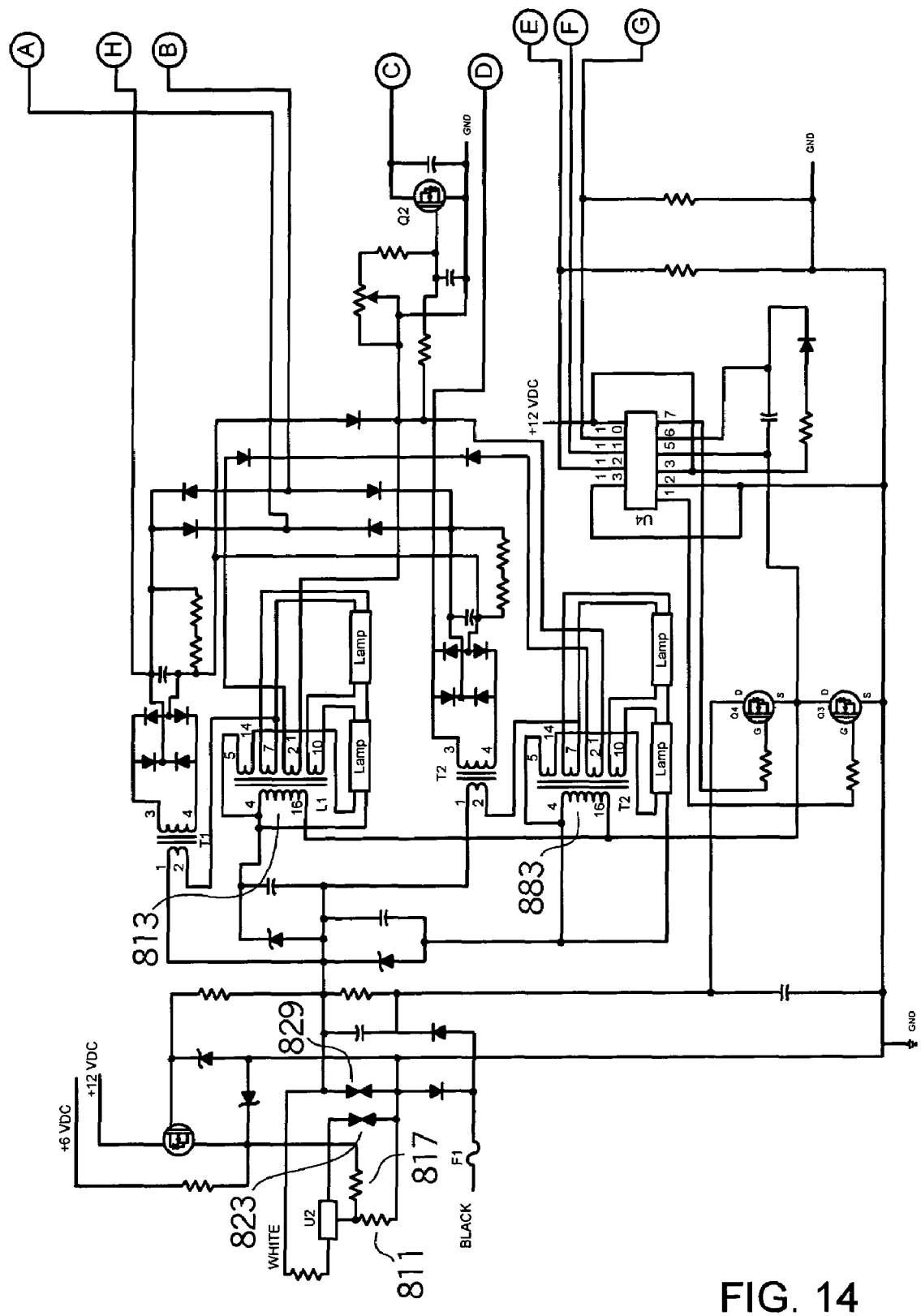
FIG. 14 illustrates a portion of an alternate controller apparatus that may be used with an embodiment of the system.
Figure 15:
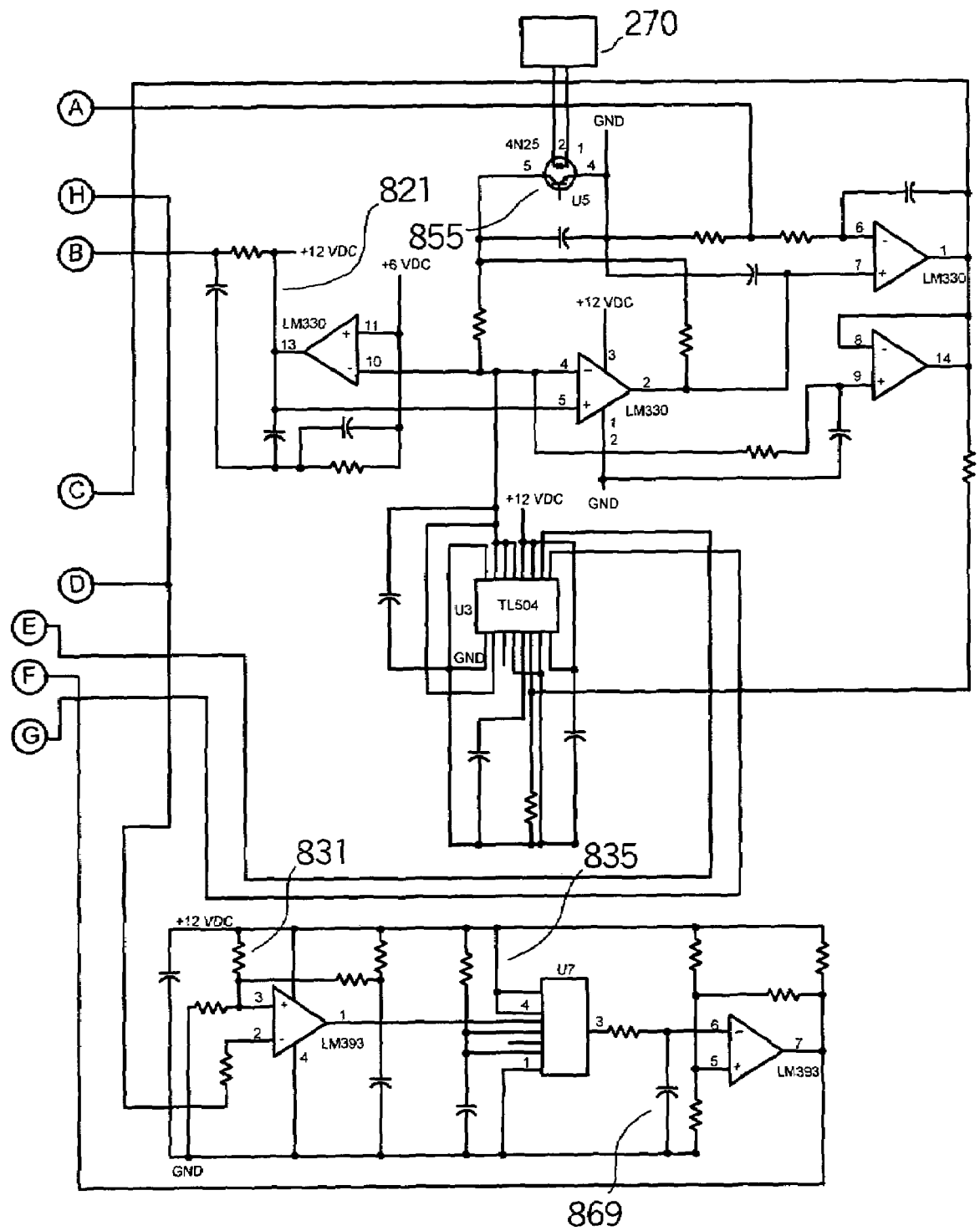
FIG. 15 illustrates additional portions of the alternate controller apparatus of FIG. 14.

FIGS. 14 and 15 illustrate an alternate driver circuit that may be used to implement the present invention. Such a circuit may include elements of a circuit such as that disclosed in U.S. Pat. No. 5,287,040, of which FIG. 2 (parts 1-4) and the accompanying text are incorporated herein by reference in all aspects. Referring to FIGS. 14 and 15, a suitable circuit may differ from that disclosed in U.S. Pat. No. 5,287,040. For example, the circuit may include a frequency injector or modulator 270 such as those described above and illustrated in FIGS. 9 and 10 in order to provide output from the bulb or bulbs at elevated wavelengths. The modulator 270 may be connected to the circuit, for example via an optical isolator 855 such as one known as a 4N25 optical isolator. In addition, various component values will differ. Referring to FIG. 14, when used with two 120-watt fluorescent bulbs, or even in certain embodiments with brighter bulbs, resistors 811 and 817 may be 100Ω and 3.32 KΩ, while capacitors 823 and 829 may be 100 μF and 820 μF. In addition, transformers 813 and 883 may be made with multistranded wire, such as the transformers disclosed in U.S. patent application Ser. No. 10/834,778, filed Apr. 29, 2004, entitled "Coil Device", which is incorporated herein by reference in its entirety. Preferably, at least the secondary winding of each transformer is made with multistranded wire. Referring to FIG. 15, resistors 831 and 835 may be 14.7 KΩ and 100 KΩ, respectively, while capacitor 869 may be 0.047 1 μF, and no resistor may be required at line 821. The value of resistor 897 may vary, or it may be replaced with a variable resistor. Such changes may permit the circuit to increase the intensity of desired wavelengths of light output. One skilled in the art will also recognize that other values are possible, and that the values may be changed depending on the desired output wavelengths and intensities. Further, not all elements of FIGS. 14 and 15 may be necessary for the application of the present invention. For example, lamp sensing circuitry and/or rectifier circuitry may not be necessary.

Referring again to FIG. 13, in an embodiment the invention uses one or more germicidal bulbs or lamps such as 91A and 92A capable of emitting ultraviolet radiation of various wavelengths. These lamps are similar to conventional germicidal ultraviolet lamps, commonly referred to by those skilled in the art as T5 bulbs. However, the bulbs maybe longer than standard T5 bulbs, which are up to 36 inches long. In one embodiment, the preferred bulbs are of a length substantially equivalent to that of a T12 bulb (i.e., approximately four feet long). The longer bulb allows a greater intensity of output than would normally be expected from a T5 bulb. The diameter of the bulb is also that of a standard T12 bulb, although each end of the bulb may be been modified to have few inches where the diameter is that of a T5 bulb. This effectively allows a T12 bulb to be inserted into T5 bulb's socket.

The bulbs may be constructed of high quality quartz or another appropriate material. It may also include a filter to absorb visible light. The gas mixture in the bulb can be the standard mixture that is expected in a germicidal ultraviolet bulb, such as a mixture containing approximately 65% argon, a percentage of krypton, and optionally a trace of mercury. The gas may be present at a pressure that elevated from the pressure of an ordinary T5 bulb by as much as four times or more. Surprisingly, although mercury-containing bulbs can be used with the present invention, I have found that a mercury-free bulb can be used in the present invention.

The lamps may include filaments. However, in an embodiment the lamps do not include filaments, thus allowing the lamps to be lit at extremely low temperatures because there is no need to heat the filament as in previous systems. Each lamp may also have two unconnected, single electrodes through which power can be supplied.

Conventional Type UV-C bulbs only deliver most intensities of ultraviolet light at a wavelength of approximately 240 to 255 nm. While some irradiance is also emitted in the visible region, the irradiance of the ultraviolet region is much higher than the irradiance of any wavelength of the visible region. With an unconventional bulb such as that described above, or with an EBBU and a conventional germicidal bulb, or with an EBBU and an unconventional bulb, a wide range of wavelengths can be used to destroy a wide variety of organisms. The use of an EBBU such as that described above allows the user to blend the output light so that ultraviolet light (i.e., that having a wavelength of approximately 254 nm) can be emitted along with light of other, preferably higher, wavelengths. The wavelengths may be selected by adjustment of the varistor in stage 50 and/or the frequency injector in stage 60 of the EBBU to deliver different output frequencies, and the particular frequency (and corresponding wavelength) that is selected will depend on the organism for which decontamination is desired.

Figure 16:
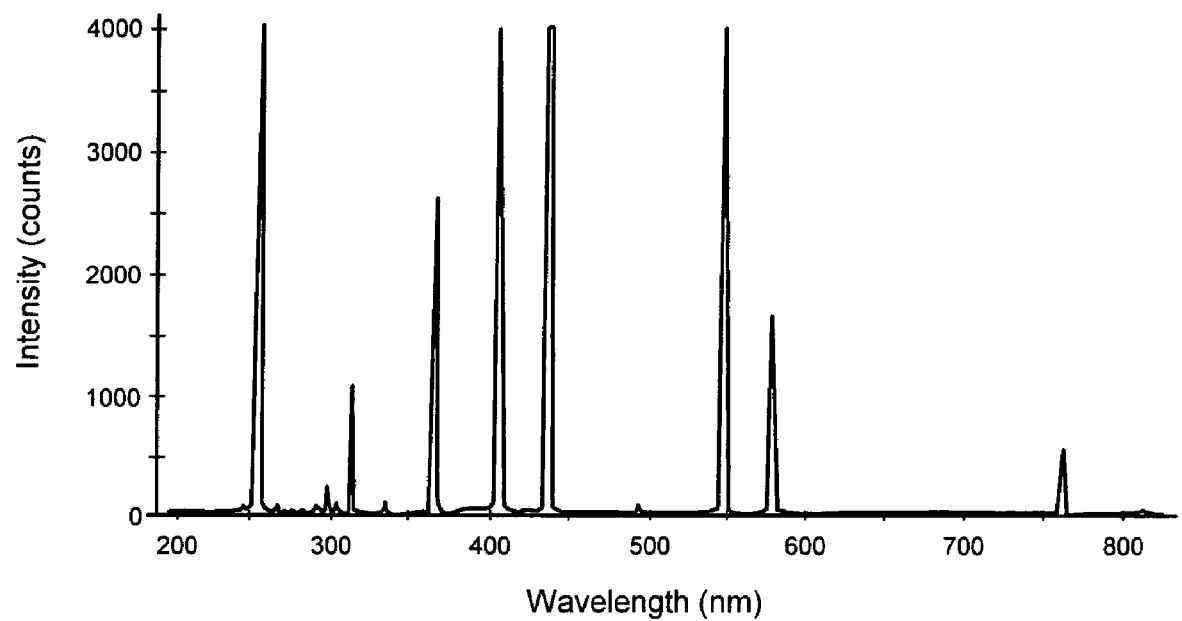
FIG. 16 illustrates the emission of light at various exemplary wavelengths to destroy various organisms and prevent them from reproducing.

For example, as illustrated in FIG. 16, I have surprisingly found that in addition to the bulb's normal operating wavelength of approximately 254 nm, the EBBU may blend the input frequencies to one or more bulbs to increase the irradiance of emitted light at wavelengths of approximately 405 nm and 422 nm to open the outer shell of some or all *bacillus* spore types. The outer shell of the niger virus can be opened by increasing the intensity of emitted light at approximately 546 and 579 nm. When performed in connection with the normal emissions of ultraviolet light at 254 nm, the higher wavelength opens the spore, such as by cracking its outer layer, skin, outer membrane, or other shell, while the ultraviolet light damages the DNA and ensures that the organism will not reproduce. Put differently, the emitted light includes radiation emitted at a frequency that is sufficient to crack a shell of an organism. With an ozone-producing bulb, additional decontamination may be possible, even if the specimen to be decontaminated is not placed directly under the bulb(s).

The bulb is powered by the EBBU to emit various wavelengths of light, and at frequencies and for various times to kill various types of spores. The specific wavelength, frequency and/or time of application can be adjusted based on the organism that is desired to be destroyed.

As described above, the bulb can be mounted in several forms, such as in a ventilator or other hooded or enclosed device. The material containing the organism, such as food, mail, and/or other material, is placed below or in close proximity to the bulb. The distance between the bulb and the material is not essential to killing the organism. However, the further that the bulb is placed away from the material, the greater amount of time that will be required to kill the organism or organisms. One skilled in the art will recognize that at some point the distance will become so great that the light from the bulb will not reach the material in any concentrated amount and thus will not likely kill the organism. The time required to kill an organism may also be dependent on the thickness of the product containing the organism, such as an envelope, air, water, soil, human or animal tissue and/or vegetables or grains.

The EBBU may take on various embodiments in addition to that described above, although in each embodiment it allows the bulb(s) to emit light at various wavelengths. In an embodiment, the EBBU is a low power device that can operate on a common 120-volt circuit (or other standard voltage circuits as necessary outside of the United States). Other designs are possible, such as a unit that will operate between 80 volts and 300 volts on a 50/60 Hz signal.

The EBBU may be used in various applications. For example, the apparatus and system may be used to kill spores in food products. It can kill bacteria and/or prevent the growth of bacteria in food products. It also may be used to kill anthrax in various applications, such as when placed in a mail sorter or other letter delivery system. It may be used to destroy germs, molds, mites, cysts, abnormal cells or other organisms. The system may be placed in water treatment plants or home water purification systems to eliminate bacteria and viruses from drinking water. It may be used to decontaminate surgical instruments and other medical equipment. Finally, the method and system can be used to decontaminate air that has passed through a decontamination system using the present invention. Additional applications not described herein are possible and considered to be within the scope of the present invention.

Example 1

In one example, an EBBU with a germicidal lamp was tested to determine the time it would take to destroy *bacillus* spores. Four spore strips were exposed to targeted ultraviolet light at zero seconds, 30 seconds, 60 seconds and 120 seconds, respectively. Each spore strip was positioned approximately nine inches from the bulb. One type of spore strip included *bacillus stearothermophilus* and was incubated at 55° C. for 14 days prior to exposure to the light. Other spore strips included *B. subrilis* var. *niger* and was incubated at 35° C. for 14 days prior to exposure to the light. At one second, the bulb output wattage varied up to approximately 190 watts. At 30 seconds, the bulb output wattage varied between 175 watts and 285 watts. At 60 seconds, the bulb output wattage varied between 182 watts and 289 watts. At 120 seconds, the bulb output wattage varied between 171 watts and 291 watts. Irradiance levels of light emitted at approximately 405 nm and 422 nm that were similar to the irradiance levels of UV-C light opened and destroyed the *bacillus* spore types, while similar combinations of UV-C and light at 405 nm and 502 nm opened and destroyed the niger virus.

It is to be understood that the invention is not limited in its application to the details of construction and to the arrangements of the components set forth in this description or illustrated in the drawings. The invention is capable of other embodiments and of being practiced and carried out in various ways. Hence, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

The invention claimed is:

1. A decontamination system, comprising:
   a power source;
   a treating area that receives an object to be decontaminated;
   a lighting controller; and
   one or more ultraviolet lamps that, when controlled by the lighting controller, will emit ultraviolet and visible light, the ultraviolet and visible light including light at one or more selected wavelengths at intensities sufficient to accelerate damage to an organism exposed to the light in the treating area.

2. The system of claim 1 wherein the one or more lamps are comprised of quartz.

3. The system of claim 1 wherein the one or more lamps contain a gas mixture comprising at least argon and krypton.

4. The system of claim 1 wherein the one or more lamps contain a gas mixture for a germicidal lamp.

5. The system of claim 1 wherein the controller includes a frequency generator that adjusts the irradiance of the light emitted so that the selected wavelengths include two wavelengths higher than 254 nm that, when the intensities of the light emitted at the selected wavelengths are increased, are sufficient to open the outer shell of a spore in the treating area.

6. The system of claim 5 wherein the frequency generator comprises a pulse width modulator.

7. The system of claim 1 wherein the controller includes one or more transformers having at least one winding comprising multistranded wire.

8. A decontamination apparatus, comprising:
   a lighting controller including a power source, a frequency generator, and an output;
   a treating area that receives an object to be decontaminated; and
   one or more fluorescent bulbs connected to receive power from the output and emit light in the ultraviolet and visible regions, the light including selected wavelengths at intensities sufficient to open a shell of an organism in the treating area.

9. The apparatus of claim 8, wherein the selected wavelengths include two wavelengths higher than that of the ultraviolet light, and the intensities of at least one of the selected wavelengths are near the intensity of the emitted ultraviolet light.

10. The apparatus of claim 8 wherein the bulbs contain a gas comprising argon and krypton.

11. The apparatus of claim 8 wherein the frequency generator adjusts the intensities of the light emitted at the selected wavelengths.

12. A lighting controller, comprising:
   a frequency generator;
   a treating area; and
   an output to receive and deliver power to one or more lamps that illuminate the treatment area;
   wherein the frequency generator adjusts the frequency of a signal delivered to the output so that, when the output is connected to one or more bulbs, the bulbs emit radiation at least two wavelengths that together will crack the shell of an organism in the treating area; and
   wherein the output also delivers power to the one or more bulbs so that the one or more bulbs will emit light at approximately 254 nm.

13. The system of claim 1, further comprising a light diffuser that directs light from one or more ultraviolet lights into the treating area.

* * * * *

UNITED STATES PATENT AND TRADEMARK OFFICE
CERTIFICATE OF CORRECTION

PATENT NO.      : 7,612,492 B2                                           Page 1 of 1
APPLICATION NO. : 10/862495
DATED           : November 3, 2009
INVENTOR(S)     : Guy J. Lestician It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1546 days.

Signed and Sealed this

Nineteenth Day of October, 2010

David J. Kappos
*Director of the United States Patent and Trademark Office*